US00PP26229P2

(12) United States Plant Patent
Ubink

(10) Patent No.: US PP26,229 P2
(45) Date of Patent: Dec. 15, 2015

(54) ***ECHEVERIA* PLANT NAMED 'APUS'**

(50) Latin Name: ***Echeveria pulidonis*×*E. elegans***
Varietal Denomination: Apus

(71) Applicant: Gert Ubink, Kudelstaart (NL)

(72) Inventor: Gert Ubink, Kudelstaart (NL)

(73) Assignee: HandelsKweKeriJ UBink B.V., Kudelstaart (NL)

( * ) Notice: Subject to any disclaimer, the term of this patent is extended or adjusted under 35 U.S.C. 154(b) by 85 days.

(21) Appl. No.: 13/998,400

(22) Filed: Oct. 29, 2013

(51) Int. Cl.
*A01H 5/00* (2006.01)

(52) U.S. Cl.
USPC ..... Plt./373

(58) Field of Classification Search
USPC ..... Plt./372, 373
See application file for complete search history.

*Primary Examiner* — Keith O. Robinson

(57) ABSTRACT

A new cultivar of *Echeveria* plant named 'Apus' that is characterized by grey-green leaves with grey-red margins and tips, a compact habit and yellow flowers.

2 Drawing Sheets

Botanical classification: *Echeveria pulidonis*×*E. elegans*.
Variety denomination: 'Apus'.

BACKGROUND OF THE INVENTION

The present invention relates to a new and distinct cultivar of *Echeveria* plant botanically known as *Echeveria pulidonis*×*E. elegans* and hereinafter referred to by the cultivar name 'Apus'.

'Apus' originated from the crossing of the female or seed parent an unnamed proprietary *Echeveria pulidonis* cultivar and the male or pollen parent an unnamed proprietary *Echeveria elegans* cultivar. The crossing was conducted in 2006 in Kudelstaart, Netherlands. The resulting seeds were subsequently planted and grown. The cultivar 'Apus' was selected by the inventor in 2008 in a controlled environment as a single plant within the progeny of the stated cross in a cultivated area of Kudelstaart, Netherlands.

Asexual reproduction of the new cultivar 'Apus' first occurred by leaf cuttings in 2008 in Kudelstaart, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Echeveria* cultivar 'Apus'. These traits in combination distinguish 'Apus' as a new and distinct cultivar apart from other existing varieties of *Echeveria* known by the inventor.

1. *Echeveria* 'Apus' exhibits grey-green leaves with grey-red margins and tips.
2. *Echeveria* 'Apus' exhibits a compact habit.
3. *Echeveria* 'Apus' exhibits yellow flowers.

The closest comparison cultivar is the co-pending application cultivar *Echeveria* 'Sagitta' (Plant patent application Ser. No. 13/998,399). 'Apus' is distinguishable from 'Sagitta' by the following characteristics:

1. *Echeveria* 'Apus' exhibits leaves that are thicker with a more rounded tip and are greyer in color than the leaves of 'Sagitta'. In comparison, the leaves of 'Sagitta' are thinner with a more pointed tip and are greener in color than the leaves of 'Apus'.

'Apus' is distinguishable from the female parent plant, an unnamed proprietary *Echeveria pulidonis* cultivar, by the following characteristics:

1. *Echeveria* 'Apus' exhibits leaves that have more grey color than the leaves of the female parent plant. The leaves of the female parent plant have more green color.
2. *Echeveria* 'Apus' exhibits a fewer number of flowering stems than the female parent plant.

'Apus' is distinguishable from the male parent plant parent plant, an unnamed proprietary *Echeveria elegans* cultivar, by the following characteristics:

1. *Echeveria* 'Apus' exhibits leaves that have more green color than the leaves of the male parent plant. The leaves of the male parent plant have more grey color.
2. *Echeveria* 'Apus' exhibits leaves that are longer in length than the leaves of the male parent plant.

BRIEF DESCRIPTION OF THE DRAWING

The accompanying photographs illustrate the distinguishing traits of *Echeveria* 'Apus'.

Figure 1:
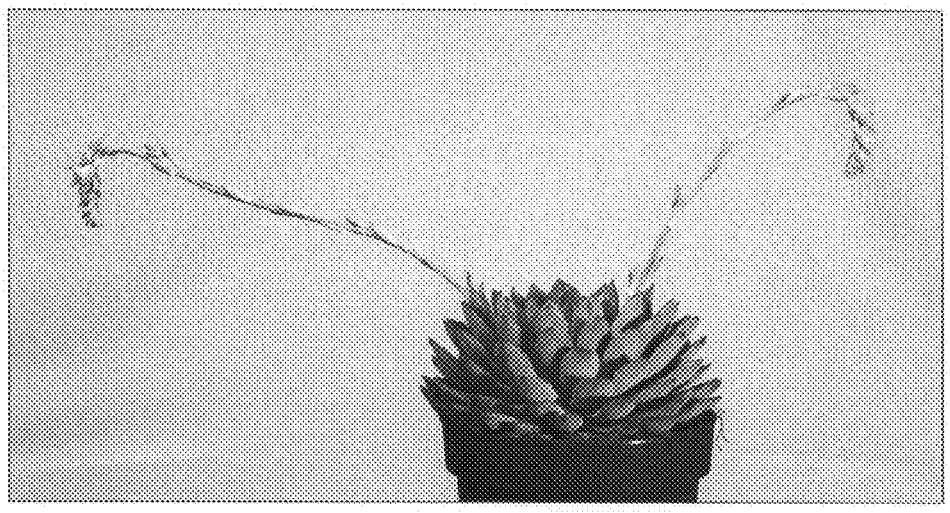
FIG. 1 shows an overall view of an 18 month old plant.
Figure 2:
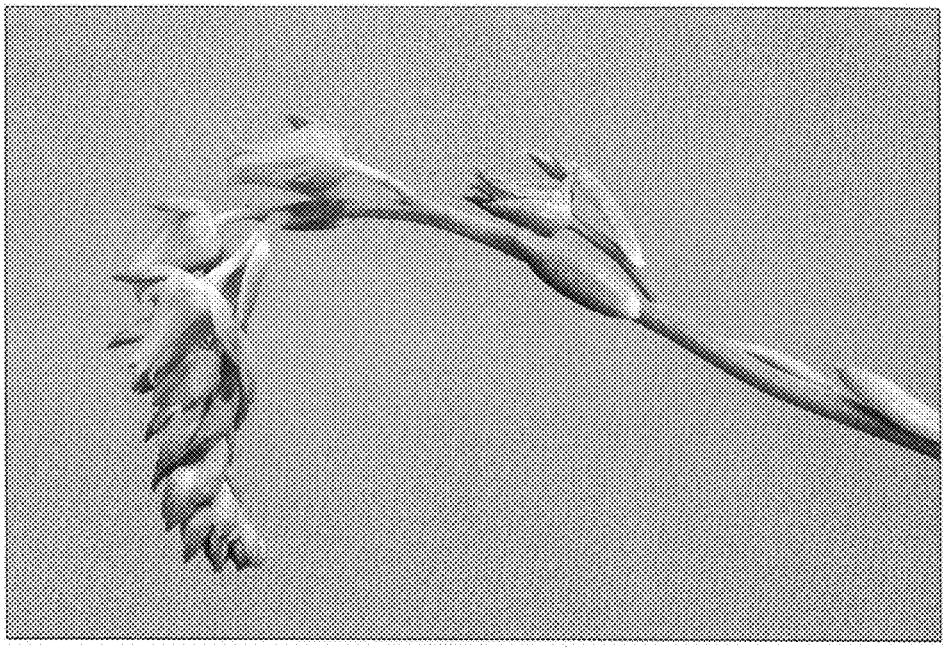
FIG. 2 shows an enlarged view of the flowers.
Figure 3:
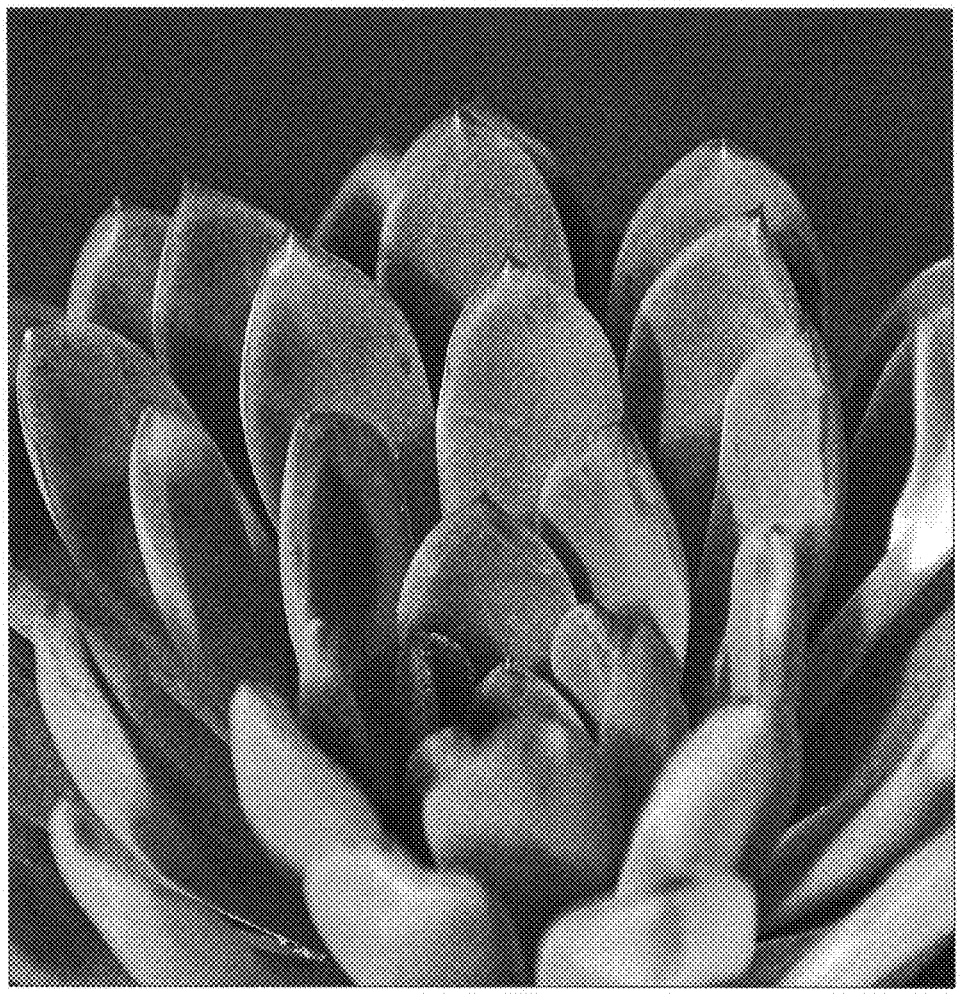
FIG. 3 shows an enlarged view of the leaves.

The photographs were taken using conventional techniques and although colors may appear different from actual colors due to light reflectance it is as accurate as possible by conventional photographic techniques.

BOTANICAL DESCRIPTION OF THE PLANT

The following is a detailed description of the new *Echeveria* cultivar named 'Apus'. Data was collected in Kudelstaart, Netherlands from 18 month old plants grown in a glass greenhouse in 17 cm. diameter containers. The time of year was Autumn and the temperature range was 18-25 degrees Centigrade during the day and 12-18 degrees Centigrade at night. The light level was natural light level. No photoperiodic treatments or growth retards were used. Color determinations are in accordance with The Royal Horticultural Society Colour Chart 2007 edition, except where general color terms of ordinary dictionary significance are used. The growing requirements are similar to the species. 'Apus' has not been tested under all possible conditions and phenotypic differences may be observed with variations in environmental, climatic, and cultural conditions, however, without any variance in genotype.

Botanical classification: *Echeveria pulidonis*×*E. elegans* 'Apus'.

Annual or perennial: Perennial.

Parentage: 'Apus' is a hybrid of the female parent an unnamed proprietary *Echeveria pulidonis* cultivar and the male parent an unnamed proprietary *Echeveria elegans* cultivar.

Plant type: Pot plant.

Plant shape: Basal rosette, non-branching.

Suitable container size: 7 cm. pots.

Plant height: 8.3 cm. to top of leaves, 20.3 cm. to top of inflorescences.

Plant width: 18.6 cm. for leaves, 33.3 cm. including inflorescences.

Vigor: Moderate.

Low temperature tolerance: 10° Centigrade.

High temperature tolerance: 40° Centigrade.

Propagation: Leaf cuttings.

Time to initiate roots (summer): 14 days at 20° C.

Time to initiate roots (winter): 21 days at 20° C.

Time to produce a rooted cutting (summer): 120 days at 20° C.

Time to produce a rooted cutting (winter): 150 days at 20° C.

Growth rate: Approximately 2.0 cm. per month.

Crop time: Approximately 5 months.

Root system: Fibrous.

Root color: N155.

Foliage:

*Leaf arrangement.*—Basal rosette, non-branching.
*Compound or single.*—Single.
*Quantity of leaves per plant.*—Average 120.
*Leaf shape.*—Oblanceolate, slightly carinate.
*Leaf apex.*—Short apiculate.
*Leaf base.*—Broad cuneate.
*Leaf dimensions.*—7.2 cm. in length and 2.4 cm. in width.
*Leaf thickness.*—0.7 cm.
*Texture.*—Glabrous both surfaces, succulent.
*Leaf aspect.*—Slightly cupped.
*Pubescence.*—Absent.
*Leaf margin.*—Entire.
*Venation pattern.*—None visible.
*Young leaf color* (*upper surface*).—191A with a thin waxy layer 188A, margins and tip 184C.
*Young leaf color* (*lower surface*).—191B with a thin waxy layer 188A, margins and tip 184C.
191B, margins and tip 184C.
*Mature leaf color* (*upper surface*).—191A with a thin waxy layer 188A, margins and tip 181C.
*Mature leaf color* (*lower surface*).—191B with a thin waxy layer 188A, margins and tip 181B.
*Leaf attachment.*—Sessile.

Flower:

*Flower arrangement.*—Compound raceme.
*Inflorescence dimensions.*—7.1 cm. in length and 3.1 cm. in width.
*Quantity of flowers per inflorescence.*—17.
*Quantity of flowers and buds per plant.*—Average 34.
*Natural flowering season.*—Continuous.
*Rate of flower opening.*—Lower flowers in raceme open first.
*Fragrance.*—Absent.
*Flower bud length.*—1.0 cm.
*Flower bud diameter.*—0.7 cm.
*Flower bud shape.*—Deltoid.
*Bud color.*—8C with tip 24B.
*Flower aspect.*—Outward to drooping.
*Flower shape.*—Campanulate.
*Flower dimensions.*—1.3 cm. in diameter and 1.4 cm. in height.
*Flower longevity.*—5 days.
*Number of petals.*—6.
*Fused or unfused.*—Base fused.
*Petal shape.*—Narrow ovate.
*Petal margin.*—Entire.
*Petal apex.*—Acute.
*Petal base.*—Fused.
*Petal texture.*—Glabrous both surfaces.
*Petal dimensions.*—1.3 cm. in length and 0.4 cm. in width.
*Petal color when opening* (*upper side*).—12A, base 12D.
*Petal color when opening* (*under side*).—12B, base 12C.
*Petal color fully opened* (*upper side*).—13A, base 12C.
*Petal color fully opened* (*under side*).—13A, base 12C.
*Petal color fading to.*—Not fading.
*Self-cleaning or persistent.*—Self-cleaning.

Sepals:

*Number of sepals.*—5.
*Sepal arrangement.*—Rotate.
*Sepal shape.*—Lanceolate.
*Sepal margin.*—Entire.
*Sepal apex.*—Acuminate.
*Sepal base.*—Cuneate.
*Sepal texture.*—Glabrous (both surfaces).
*Sepal dimensions.*—7.5 mm. in length and 2 mm. in width.
*Immature sepal color* (*inner side*).—191A with a thin waxy layer 188A.
*Immature sepal color* (*under side*).—191A with a thin waxy layer 188A.
*Mature sepal color* (*inner side*).—191A with a thin waxy layer 188A.
*Mature sepal color* (*under side*).—191A with a thin waxy layer 188A.

Calyx:

*Calyx dimensions.*—5 mm. in length and 13 mm. in diameter.

Scape:

*Scape dimensions.*—30.5 cm. in length and 4 mm. in diameter.
*Scape angle.*—45 degrees.
*Scape strength.*—Moderately strong.
*Scape texture.*—Smooth.
*Scape color.*—177D.

Peduncle:

*Peduncle dimensions.*—2.3 cm. in length and 2 mm. in diameter.
*Peduncle angle.*—40 degrees.
*Peduncle strength.*—Moderately strong.
*Peduncle texture.*—Smooth.
*Peduncle color.*—177D.

Pedicels:

*Pedicel dimensions.*—8 mm. in length and 1.5 mm. in diameter.

*Pedicel strength.*—Moderate.

*Pedicel texture.*—Smooth.

*Pedicel angle.*—40 degrees.

*Pedicel color.*—148D.

Reproduction organs:

*Stamen number.*—Average 12.

*Anther shape.*—Basifixed, narrow ovate.

*Anther length.*—1.0 mm.

*Anther color.*—148D.

*Filament length.*—5.0 mm.

*Filament color.*—12C.

*Amount of pollen.*—Moderate.

*Pollen color.*—157A.

*Pistil number.*—Average 5.

*Pistil length.*—4.0 mm.

*Stigma shape.*—Pointed.

*Stigma color.*—143A.

*Style length.*—3 mm.

*Style color.*—144A.

*Ovary color.*—157D.

Fruit and seed: Fruit or seed production has not been observed.

Disease and pest resistance: Disease and pest resistance has not been observed.

The invention claimed is:

1. A new and distinct variety of *Echeveria* plant named 'Apus' as described and illustrated.

* * * * *